US009566272B2

(12) United States Patent
Winckle et al.

(10) Patent No.: US 9,566,272 B2
(45) Date of Patent: *Feb. 14, 2017

(54) COMPOSITIONS AND METHODS FOR TREATING DISEASES OF THE NAIL

(71) Applicant: Dow Pharmaceutical Sciences, Inc., Petaluma, CA (US)

(72) Inventors: Gareth Winckle, Biot (FR); Gregory T. Fieldson, Morgantown, WV (US)

(73) Assignee: DOW PHARMACEUTICAL SCIENCES, INC., Petaluma, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/755,699

(22) Filed: Jun. 30, 2015

(65) Prior Publication Data
US 2015/0374679 A1 Dec. 31, 2015

Related U.S. Application Data

(63) Continuation of application No. 12/006,531, filed on Jan. 3, 2008, now abandoned.

(51) Int. Cl.
*A61K 31/454* (2006.01)
*A61K 9/00* (2006.01)
*A61K 47/10* (2006.01)
*A61K 47/14* (2006.01)
*A61K 47/24* (2006.01)
*A61K 8/49* (2006.01)

(52) U.S. Cl.
CPC ........... *A61K 31/454* (2013.01); *A61K 9/0014* (2013.01); *A61K 47/10* (2013.01); *A61K 47/14* (2013.01); *A61K 47/24* (2013.01); *A61K 8/496* (2013.01)

(58) Field of Classification Search
CPC .... A61K 2300/00; A61K 47/10; A61K 33/00; A61K 47/14; A61K 47/44; A61K 9/06; A61K 9/08
See application file for complete search history.

(56) References Cited

U.S. PATENT DOCUMENTS

| 5,874,069 A | 2/1999 | Mendolia et al. |
| 6,538,039 B2 | 3/2003 | Laurent |
| 6,585,963 B1 | 7/2003 | Quan et al. |
| 6,740,326 B1 | 5/2004 | Meyer et al. |
| 7,214,506 B2 | 5/2007 | Tatsumi |
| 7,622,844 B1 | 11/2009 | Kuhlmann-Wilsdorf |
| 8,039,494 B1 * | 10/2011 | Winckle ............... A01N 43/653 514/359 |
| 2003/0082129 A1 | 5/2003 | Buckingham et al. |
| 2004/0180025 A1 | 9/2004 | Long et al. |
| 2005/0142094 A1* | 6/2005 | Kumar ................. A61K 8/0212 424/70.14 |
| 2005/0186161 A1 | 8/2005 | Kawase |
| 2005/0244342 A1 | 11/2005 | Friedman et al. |
| 2006/0110415 A1 | 5/2006 | Gupta |
| 2006/0147383 A1 | 7/2006 | Mallard |
| 2006/0280706 A1 | 12/2006 | Sebillotte-Arnaud |
| 2007/0041910 A1 | 2/2007 | Pitre |
| 2007/0071705 A1 | 3/2007 | De Oliveira et al. |
| 2007/0082375 A1* | 4/2007 | Tatsumi ............. A61K 31/4196 435/32 |
| 2007/0142317 A1 | 6/2007 | Warren et al. |
| 2007/0207222 A1 | 9/2007 | Yu et al. |

FOREIGN PATENT DOCUMENTS

| GB | 2 407 496 | 10/2003 |
| JP | 2002-524495 A | 8/2002 |
| WO | 2004/021968 A2 | 3/2004 |
| WO | 2004/084826 | 10/2004 |
| WO | 2007/070643 A2 | 6/2007 |

OTHER PUBLICATIONS

Japan Pharmaceutical Excipients Council, Revised Pharmaceutical Additives Handbook, Yakuji Nippo Limited, Feb. 28, 2007, pp. 407-408.

Tatsumi, Yoshiyuki et al., "Therapeutic Efficacy of Topically Applied KP-103 against Experimental Tinea Unguium in Guinea Pigs in Comparison with Amorolfine and Terbinafine," Antimicrobial Agents and Chemotherapy, Dec. 2002, vol. 46, No. 12, pp. 3797-3801.

* cited by examiner

*Primary Examiner* — Mark V Stevens
(74) *Attorney, Agent, or Firm* — Kilpatrick Townsend & Stockton LLP

(57) ABSTRACT

Methods and compositions for treating disorders of the nail and nail bed. Such compositions contain a vehicle in which all components of the composition are dissolved, suspended, dispersed, or emulsified, a non-volatile solvent, a wetting agent, and a pharmaceutically active ingredient that is soluble in the non-volatile solvent and/or a mixture of the vehicle and the non-volatile solvent, and which composition is effective in treating a disorder of the nail or nail bed.

4 Claims, 2 Drawing Sheets

COMPOSITIONS AND METHODS FOR TREATING DISEASES OF THE NAIL

CROSS REFERENCE TO RELATED APPLICATIONS

The present application claims the benefit of U.S. application Ser. No. 12/006,531, filed Jan. 8, 2008, which is hereby incorporated by reference for all purposes.

FIELD OF THE INVENTION

The invention pertains to the field of treatment of diseases of the nail and nail bed. In particular, the invention pertains to methods for treatment of disorders such as onychomycosis or psoriasis involving the nails.

BACKGROUND OF THE INVENTION

Onychomycosis, a fungal disease of the nail unit caused by yeasts, dermatophytes, or other molds, accounts for approximately 50% of all nail disorders in humans. In about 80% of onychomycosis cases, the toenails are infected, whereas in the remaining 20%, the fingernails are infected. The symptoms of this disease include split, thickened, hardened, and rough nail plates.

Another common disorder of nails is nail psoriasis, which affects up to 50% of patients with psoriasis. Characteristic nail psoriasis symptoms include pitting, which appears as punctuated or irregularly shaped depressions arranged on the surface of the body of the nail; discoloration of the nail bed; onycholysis or detachment of the body of the nail from the nail bed; subungual keratosis; or anomalies of the body of the nail. Other diseases and disorders involving the nails in humans and in other animals include onychia, onychocryptosis, onychodystrophy, onychogryposis, onycholysis, onychomadesis, onychophosis, onychoptosis, paronychia, koilonychia, subungual hematoma, and laminitis.

The nail plate is thick, hard, and dense, and represents a formidable barrier to drug penetration. Although nail material is similar in various ways to the stratum corneum of the skin, the nail is composed primarily of hard keratin which is highly disulfide-linked and is approximately 100-fold thicker than stratum corneum.

Various topical therapies have been suggested for treatment of nail disorders, such as onychomycosis. Nail lacquers, coating, polishes, enamels, and varnishes have been described. Bohn, U.S. Pat. No. 4.957,730, describes a nail varnish containing a water-insoluble film-forming substance and antimycotic compound. Ferro, U.S. Pat. No. 5,120,530, describes an antimycotic nail varnish containing amorolfine in quaternary ammonium acrylic copolymer. The water-insoluble film former is a copolymerizate of acrylic acid esters and methacrylic acid esters having a low content of quaternary ammonium groups. Bohn, U.S. Pat. No. 5,264,206, describes a nail lacquer with antimycotic activity, which contains an antimycotic agent and water-insoluble film formers including polyvinyl acetate, a copolymer of polyvinyl acetate and acrylic acid, copolymers of vinyl acetate and crotonic acid. Wohlrab, U.S. Pat. No. 5,346,692, describes a nail lacquer for treating onychomycosis, comprised of a film-forming agent, an antimycotically active substance, and urea, wherewith the antimycotic agent and urea are liberated from the lacquer when the lacquer is applied. A preferred formulation comprises cellulose derivatives as film former, clotrimazole as the antimycotic agent, dibutyl phthalate as a plasticizer, and a mixture of acetone and ethanol as solvent. Nimni, U.S. Pat. No 5,487,776, describes a nail lacquer composition which forms a water permeable film containing griseofulvin when the organic solvent system evaporates, wherein a portion of the griseofulvin is in solution and a portion of griseofulvin is present as a colloidal suspension. Chaudhuri, U.S. Pat. No. 6,143,794, describes a topical formulation for the treatment of nail fungal infections that includes an antifungal, solvent, gelling agent, adhesion-promoting agent, film-forming agent, surfactant, and optionally a keratolytic agent. The adhesion-promoting agent was a hydroxy-terminated polyurethane such as polyolprepolymer-2. All of these patents and publications describe products applied to the nail that form a substantive nail coating or film containing a drug from which the drug is to penetrate into the nail. None of these methods has proven to be consistently effective in treating disorders of the nail such as onychomycosis.

Various topical therapies utilizing chemical compounds disclosed to enhance penetration through the nail have been described. Knowles, U.S. Pat. No. 5,652,256, describes the use of methyl acetate as a penetration enhancing compound in combination with naftifine or sulconazole and naftifine as a topical gel for fungal treatment of the nails. Sorenson, U.S. Pat. No. 5,972,317, discloses that a proteolytic enzyme such as papain, delivered by pads soaked in the enzyme solution, produces a more permeable nail. Sun, U.S. Pat. No. 6,231,875, describes acidified compositions of antifungals to enhance transport across nails and skin. Reeves, U.S. Pat. No. 6,391,879, describes the combination of an anti-fungal agent dissolved in an anhydrous blend of polyglycol and DMSO. Although these and other enhanced penetration formulations were reported to increase penetration through the nail, they have not been shown to be clinically effective in treating conditions of the nail, such as onychomycosis.

Because of the difficulty in obtaining clinically effective concentrations of medication to the nail bed by topical application of a pharmaceutical composition to the affected nail, nail disorders, such as onychomycosis, are typically treated with systemic medications or with topical medications following removal of the nail. Systemic treatment for onychomycosis and other nail disorders is often not satisfactory because therapy must be continued for long periods of time, often many weeks or months, and the medication has effects on tissues other than on the affected nail. Antifungal compounds, such as miconazole and ketoconazole, have been demonstrated to be effective in topically treating onychomycosis after nail removal. However, it is clear that removal of the nail is a measure than most individuals suffering from onychomycosis would prefer not to undergo if a less drastic therapeutic method would be efficacious.

Pitre, U.S. Patent Publication 2007/0041910, filed as U. S. patent application Ser. No. 11/432,410; and Mallard, U.S. Patent Publication 2006/0147383, filed as U.S. patent application Ser. No. 11/315,259, disclose that application of a pharmaceutical composition containing a vehicle, a volatile silicone, and a non-volatile oily phase, provides increased penetration of a pharmaceutically active compound when topically to skin or mucous membrane. This enhanced penetration is obtained without the use of glycols, such as propylene glycol, which are known to augment skin penetration of pharmaceutical compounds but which are also known to be irritating to skin. The formulations of Pitre and Mallard contain at least 25% w/w of a volatile silicone and, if formulated with an alcoholic vehicle, contain at least 15% of alcohol. All alcoholic compositions disclosed in Pitre and Mallard contain greater than 50% volatile silicone and the concentration of the volatile silicone is at least twice the concentration of the alcohol in the composition.

Pitre and Mallard do not disclose or suggest the use of such compositions for the treatment of diseases of a nail, such as onychomycosis. Moreover, studies have been conducted, including studies conducted in the laboratories of the present inventors, that show that the penetrating ability of an active agent from a composition into skin cannot be correlated to the penetrating ability of the active agent from the composition into or through a nail.

A significant need remains for a pharmaceutical composition that provides for enhanced penetration of a pharmaceutical agent contained within the composition into and through an intact nail. Such a composition would be valuable for topically treating conditions affecting the nail or nail bed, such as onychomycosis.

DESCRIPTION OF THE INVENTION

Figure 1:
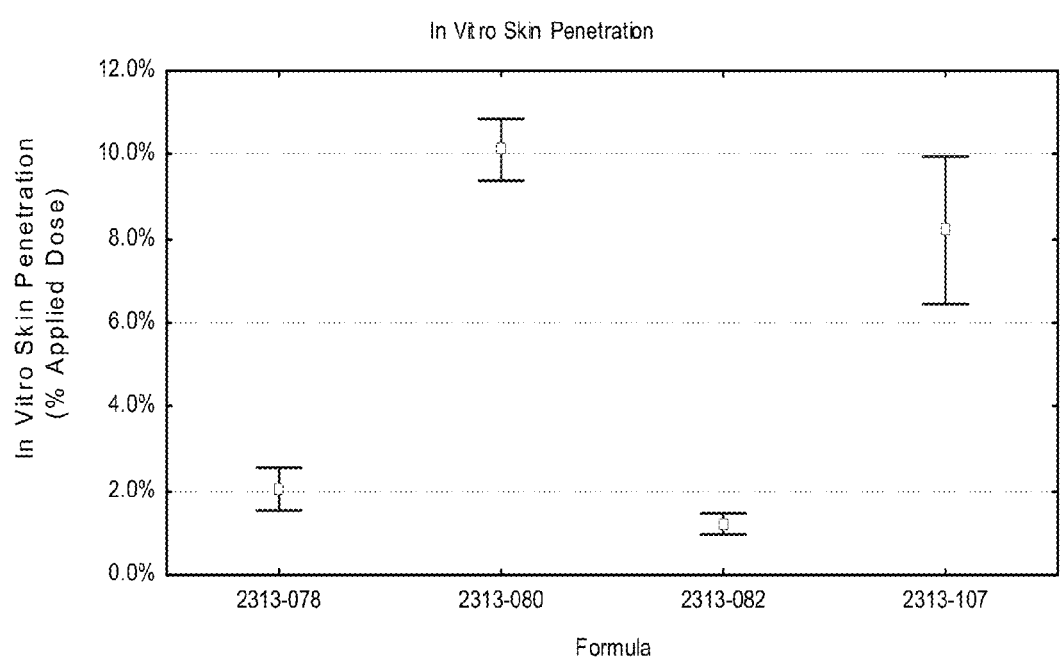
FIG. 1 is a graph showing the in vitro penetration of KP-103 through skin from a formulation of the invention and from three prior art formulations.

It has been unexpectedly discovered that a pharmaceutical composition containing an active pharmaceutical ingredient (API), a solvent, referred to herein as the "vehicle" or the "volatile vehicle", a wetting agent which may or may not be the same compound as the vehicle, and a non-volatile solvent which has limited water miscibility provides enhanced penetration of the API into and through an intact nail. Preferably, the composition of the invention is free of film forming polymeric compounds. It is conceived that such compositions may be used to deliver an API in order to treat medical conditions involving the nail and/or the underlying nail bed.

In one embodiment, the invention is a pharmaceutical composition for the treatment of disorders of the nail or nail bed. The pharmaceutical composition of the invention contains a volatile and/or penetrating vehicle, a non-volatile solvent that is dissolved, suspended, dispersed, or emulsified within the vehicle, an API that is soluble in the non-volatile solvent and/or a mixture of the vehicle and the non-volatile solvent and is optionally soluble in the vehicle, and a wetting agent, which may or may not be the vehicle itself.

In another embodiment, the invention is a pharmaceutical formulation for delivery of an API to the nail or nail bed in order to treat disorders of this area. According to this embodiment, the formulation contains a volatile and/or penetrating vehicle, a non-volatile solvent that is dissolved, suspended, dispersed, or emulsified within the vehicle, and a wetting agent, which may or may not be the vehicle itself. The API that is to be used with the formulation of the invention is one that is soluble in the non-volatile solvent and/or a mixture of the vehicle and the non-volatile solvent and is optionally soluble in the vehicle alone.

In another embodiment, the invention is a method for treating a disorder of the nail or nail bed. According to this embodiment of the invention, a pharmaceutical composition containing a volatile and/or penetrating vehicle, a non-volatile solvent that is dissolved, suspended, dispersed, or emulsified within the vehicle, an API that is soluble in the non-volatile solvent and/or a mixture of the vehicle and the non-volatile solvent and is optionally soluble in the vehicle alone, and a wetting agent, which may or may not be the vehicle itself, is topically applied to the surface of a nail that is suffering from a disorder in an amount and for a time sufficient to ameliorate the symptoms of the disorder.

As used herein, the term "volatile" when referring to the vehicle means that the vehicle is a compound that evaporates from the surface of the nail when applied. Volatile vehicles are compounds which have a measurable vapor pressure, and preferably are compounds that have a vapor pressure of greater than 100 Pa at room temperature. Examples of volatile vehicles include: acetone, 2-amino-2-methyl-1-propanol, 1,2-butanediol, 1,4-butanediol, 2-butanol, cyclomethicone-4, cyclomethicone-5, cyclomethicone-6, ethanol, ethyl acetate, n-heptane, isobutanol, isopropyl alcohol, 1-propanol and 2-propanol.

As used herein, the term "penetrating" when referring to the vehicle means that the vehicle is a compound that rapidly penetrates into a nail when applied to the surface of the nail so that, after 10 minutes following the application of a thin layer of the vehicle onto the surface of a nail, no more than 10% of the applied amount remains on the nail surface. The term "penetrating" thus includes both volatile and non-volatile vehicles.

Examples of pharmaceutical compositions that may be used in the method of the present invention are disclosed in Pitre, U.S. patent application Ser. No. 11/432,410; and in Mallard, U.S. patent application Ser. No. 11/315,259, which applications are incorporated herein in their entirety. In accordance with the present invention, the pharmaceutical compositions of Pitre and Mallard that may be used to treat medical conditions of the nail in accordance with the present invention may contain Vitamin D as the API as disclosed in Pitre or clobetasol as disclosed in Mallard, or may contain other APIs in place of, or in addition to, these APIs, as disclosed herein.

The API of the composition of the invention is one that is useful in the treatment of a disorder of the nail or nail bed. The API is soluble in the solvent of the composition and/or in the combination of the solvent and vehicle of the composition. Examples of suitable APIs include anti-inflammatory agents, antimicrobial agents such as antibiotics and antifungal agents, anesthetic agents, steroidal agents, vitamins and derivatives thereof, anti-psoriatic drugs, and analgesic agents.

In a preferred embodiment, the API of the composition of the invention is an antifungal chemical compound, particularly those effective in the treatment of onychomycosis. Examples of suitable antifungal agents include polyene antimycotic agents such as natamycin, rimocidin, filipin, nystatin, and amphotericin B; imidazole compounds such as miconazole, ketoconazole, clotrimazole, econazole, bifonazole, butoconazole, fenticonazole, isoconazole, oxiconazole, sertaconazole, suconazole, and tioconazole; triazole compounds such as fluconazole, itraconazole, ravuconazole, posaconazole, voriconazole, (2R,3R)-2-(2,4-difluorophenyl)-3-(4-methylenepiperidine-1-yl)-1-(1H-1,2,4-triazole-1-yl)butane-2-ol (referred to herein as "KP-103"), and terconazole; allylamine compounds such as terbinafine, amorolfine, naftifine, and butenafine; echinocandin compounds such as anidulafungin, caspfungin, and micafungin; and other antifungal drugs such as ciclopirox, flucytosine, griseofulvin, gentian violet, haloprogin, tolnaftate, and undecylenic acid. Any antifungal compound suitable for pharmaceutical use in humans or mammals, and particularly those which are active in vitro against *Candida albicans*, *Trichophyton rubrum* or *Trichophyton mentagrophytes*, is suitable for the API of the invention. Particularly preferred are antifungal APIs that have relatively low binding to keratin, such as triazole compounds like KP-103.

Other APIs that are suitable for the composition of the invention include those that are effective in treating diseases and disorders of nails other than onychomycosis, especially those diseases and disorders affecting tissues deep to the external surface of the nail, such as the internal portion of the nail, the deep nail surface adjacent to the nail bed, and the nail bed. Such diseases and disorders may include onychia, onychocryptosis, onychodystrophy, onychogryposis, onycholysis, onychomadesis, onychophosis, onychoptosis, paronychia, koilonychia, subungual hematoma, and laminitis.

The vehicle of the composition of the invention is a pharmaceutically acceptable vehicle in which the constituents of the composition of the invention can be dissolved, suspended, disbursed, or emulsified. The constituents of the composition may be all within a single phase in the vehicle. For example, the API, wetting agent, and the non-volatile phase may be dissolved in the vehicle. Alternatively, the constituents may occupy separate phases within the vehicle. For example, the API may be dissolved in the vehicle and the other constituents may be suspended, dispersed, or emulsified in solvent. For another example, the API may be dissolved in the solvent which is suspended, dispersed, or emulsified in the vehicles, with the remaining constituents being dissolved in either the vehicle or the solvent. Preferably, but not necessarily, the API, wetting agent, and non-volatile phase are all miscible in the vehicle.

Examples of suitable vehicles include one or more of water, alcohols, polyols, ethers, esters, aldehydes, ketones, fatty acids, fatty alcohols, and fatty esters. Specific examples of suitable vehicles include ethanol; 3-propanediol; 1,2-butanediol; 1,2,3-propanetriol;1,3-butanediol; 1,4-butanediol; isopropyl alcohol; and 2-amino-2-methyl-1-propanol. In a preferred embodiment, the vehicle is an alcohol, and most preferably a linear or branched aliphatic lower alcohol, such as methanol, ethanol, propanol, or isopropanol.

The wetting agent of the composition of the invention is a chemical compound that reduces the surface tension of liquid compositions and that does not build viscosity. The wetting agent may be a surfactant, which may be anionic, cationic, or non-ionic.

Preferably, the wetting agent is a volatile silicone. Such volatile silicones include linear or cyclic polyorganosiloxane compounds of formula $[R_1SiOR_2]_n$ wherein n=6 or less and $R_1$ and $R_2$ are alkyl groups that may be the same or different, and which compound has a measurable vapor pressure under ambient conditions. Preferably, n=from 3 to 6, and most preferably n=4 or 5. Preferably $R_1$ and $R_2$=methyl.

Examples of cyclic volatile silicones include polydimethylcyclosiloxanes, generally known as cyclomethicones. Particular examples of cyclic volatile silicones include cyclopentasiloxane, cyclotetrasiloxane, decylmethylcyclopentasiloxane, and octylmethylcyclotetrasiloxane. Examples of linear volatile silicones include linear polysiloxanes. Particular examples of linear volatile silicones include hexamethyldisiloxane, octamethyltrisiloxane, and dimethicones.

In one particular embodiment of the invention, a single compound forms both the vehicle and the wetting agent of the composition. For example, the vehicle may be a volatile silicone. In this situation, the volatile silicone may also be the wetting agent of the composition. In the case in which the wetting agent serves also as the vehicle, the concentration of the wetting agent in the composition is sufficiently high to function as a vehicle in which all other components of the composition are dissolved, suspended, dispersed, or emulsified.

The non-volatile solvent of the composition is a non-aqueous solvent that may or may not be soluble or miscible in the vehicle of the composition. The API of the composition is preferably, but not necessarily, soluble in the non-volatile solvent. In a preferred embodiment wherein the API is hydrophilic, the non-volatile solvent is a polar or semi-polar molecule. In another preferred embodiment wherein the API is hydrophobic, the non-volatile solvent is non-polar.

Suitable non-volatile solvents for hydrophobic drugs are disclosed in Pitre, U.S. patent application Ser. No. 11/432,410 in paragraphs 0069 to 0082, which paragraphs are incorporated herein by reference. For example, the non-volatile solvent may be an ester of the formula RCO—OR', wherein R and R' may be identical or different and each of R and R' represents a linear or branched chain of an alkyl, alkenyl, alkoxycarbonylalkyl, or alkoxycarbonyloxyalkyl radical having from 1 to 25 carbon atoms, preferably from 4 to 20 carbon atoms. The non-volatile solvent may be a glyceryl ester of a fatty acid, such as fatty esters of natural fatty acids or triglycerides of animal or plant origin. The non-volatile solvent may be a fatty acid glyceride, including synthetic or semi-synthetic glyceryl esters, such as fatty acid mono-, di-, or triglycerides, which are oils or fats. The non-volatile solvent may be a non-volatile hydrocarbon, such as paraffins, isoparaffins, and mineral oil. The non-volatile solvent may be a guerbet ester. The non-volatile solvent may be a non-volatile silicone, provided that the presence of the non-volatile silicone in the composition does not result in the formation of a hard polymeric film upon application of the composition onto a nail. Included within such non-film forming silicones are polyorganosiloxane compounds that have the formula $[R_1SiOR_2]_n$ wherein n>6 and $R_1$ and $R_2$ are alkyl groups that may be the same or different, and which compound may or may not have a measurable vapor pressure under ambient conditions.

Other examples of suitable non-volatile solvents for hydrophobic drugs in addition to those disclosed in Pitre include squalane, dibutyl sebacate, isopropyl laurate, isopropyl myristate, isopropyl palmitate, isopropyl strearate, myristyl alcohol, oleyl alcohol, oleic acid, lauryl lactate, myristyl lactate, mixed C12-15 alkyl lactates, diisopropyl adipate, octyldodecanol, caproic acid, caprylic acid, capric acid, lauryl benzoate, myristyl benzoate, mixed C12 15 alkyl benzoates, benzyl benzoate, tridecyl neopentanoate, spermaceti, petrolatum, and alpha terpineol. Examples of suitable non-volatile solvents for hydrophilic drugs include diethylene glycol monoethyl ether, n-methyl pyrrolidone, dimethyl sulfoxide, ethyl lactate, hexylene glycol, glycerol, benzyl alcohol and glycerol triacetate.

The composition of the invention may contain additional optional components, such as wetting agents, preservatives, stabilizers, lubricants, humectants, moisture regulators, foaming agents, binders, pH regulators, osmotic pressure modifiers, emulsifiers, antioxidants, colors, fragrances, or odor maskers. If desired, the composition may also contain additional nail modifiers or penetration enhancers, such as urea, propylene glycol, sodium lauryl sulfate, and glycolic acid.

The composition is intended to remain in a liquid or semi-solid state after application to the nail and does not form a hard lacquer, shell, or film on the nail following application, which occurs by a process of solvent casting following evaporation of a volatile solvent which leaves behind a solid residue that forms the lacquer, shell or film. Therefore, it is preferred that the components of the composition are miscible in the composition and also are miscible in the "secondary" composition that remains after the volatile vehicle has evaporated or penetrated the nail. It is also suitable for the components of the composition, other than the vehicle, to be suspendible, dispersible, or emulsifiable, in the secondary composition, such as in the non-volatile solvent.

The composition of the invention may be prepared in any number of forms, such as ointments, creams, milks, salves, impregnated pads, solutions, tinctures, liniments, liquids, sprays, foams, suspensions, lotions, or patches. The composition may be formulated to provide for immediate or controlled release of the API from the composition.

The concentration of the various essential and optional components of the composition of the invention will vary, depending on the particular components contained in the composition, the form of the composition, the particular disease or condition that is to be treated with the composition, and whether the formulation is for immediate or for controlled release.

The API of the composition is at a concentration that is effective to treat a disorder or disease of the nail or nail bed. Typically, the concentration of the API will constitute between 0.0001 to 30% or higher by weight of the composition.

The concentration of the wetting agent in the composition may vary depending on several factors, including the identity of the wetting agent and whether the wetting agent is also the vehicle of the composition. Generally, the concentration of the wetting agent, such as a volatile silicone, will be between 0.001% to 95% by weight of the composition. Preferably, the concentration of the wetting agent is between 5% and 80%, more preferably between 7% and 60%, and most preferably between 10% and 40% w/w of the composition. In a particularly preferred embodiment, the concentration of wetting agent in the composition is between 10% and 15% w/w. In the case where the wetting agent is not functioning as a vehicle of the composition, the concentration of wetting agent in the composition will generally be towards the lower end of the above range of concentration, such as between 0.001% and 10%.

The concentration of the non-volatile solvent will constitute between 5 and 90% w/w of the composition. Generally, with less viscous forms of the compositions, lower concentrations of non-volatile phase will be present, and with more viscous forms, higher concentrations of the non-volatile phase will be used. Also, ointment and other predominately oil-based compositions tend to have a higher concentration of non-volatile phase or components than do compositions such as sprays, gels, and lotions and so will have a higher concentration of a non-volatile solvent. Typical concentrations of non-volatile solvent are between 10 and 80%, with preferred concentrations being between 12 and 60%, and most preferred concentrations between 15 and 50% w/w.

The concentration of the vehicle will be that which is sufficient to dissolve, suspend, disperse, or emulsify the other components of the composition. In many but not all cases, the concentration of the vehicle will be higher than that of any other constituent of the composition. In some cases, the concentration of the vehicle will be higher than that of the combined concentration of the other constituents of the composition. In a preferred embodiment in which the vehicle is an alcohol, the composition will contain at least 10% alcohol, more typically at least 15% alcohol, and most typically at least 25% alcohol. The concentration of alcohol in the composition may be as high as 80%, or higher. In one preferred embodiment, the concentration of alcohol is at least 50% w/w of the composition.

In a particularly preferred embodiment of the invention, the composition of the invention is an alcoholic composition containing a volatile silicone. In a first preferred embodiment, the ratio of alcohol to volatile silicone in the composition % w/w is at least 2:3, preferably at least 1:1, more preferably at least 2:1, and most preferably at least 3:1. In a second preferred embodiment, the concentration of the volatile silicone in the composition is less than 25% w/w. In a third preferred embodiment, the concentration of the alcohol in the composition is at least 40%, more preferably at least 45%, and most preferably at least 50% w/w. The composition of the invention, according to this embodiment of the invention, may be made so as to encompass any one, two, or all three of the embodiments described above. It has been determined that, when applied to the surface of a nail, the alcoholic composition of the invention containing a volatile silicone provides a high degree of penetration of an API contained therein into the nail.

Although the compositions of the invention may be used to treat various diseases and disorders of the skin or mucous membranes, they are most advantageously used to treat conditions involving the nails of the hands or feet. The compositions and methods of the invention provide increased penetration of API in the composition into and through the nail and to the nail bed. The compositions of the invention may be used effectively to treat diseases and disorders in humans or in other animals, such as cats, dogs, horses, cattle, sheep, goats, pigs, and birds. In human and in veterinary patients, the compositions of the invention may be used, depending on the particular animal treated, to treat conditions involving nails, hooves, horns, or beaks.

The compositions of the invention are especially well suited for the treatment of onychomycosis and other disorders of the nail and nail bed. The composition is topically applied to the surface of the nail and surrounding tissue by any means by which the composition may be applied. The method of application may vary depending on the physical state of the composition, whether it is in a liquid, semisolid, or solid form, and on the viscosity of the composition if it is a liquid. Thus, for example, the composition may be rubbed, painted, dabbed, dripped, sprayed, wiped, spread, or poured onto the affected nail and surrounding tissues, or utilized as a soak. Frequency of treatment and duration of therapy will very depending on several factors, including the condition that is being treated, the identity and concentration of the API in the composition, and constituents of the composition other than the API. Typically, the frequency of treatment will be twice daily to once weekly, and preferably once daily.

To further illustrate the invention, the following examples are provided. It is to be understood that these examples are provided for illustrative purposes and are not to be construed as limiting the scope of the invention.

EXAMPLE 1

Skin Penetration Study

Four different formulations were tested to determine the penetrability of an API into skin. The formulations each contained 5.00% w/w of a triazole antifungal API compound, KP-103. The compositions of the four formulations are shown in Table 1. All concentrations of the components of the formulations are in % w/w.

TABLE 1

| Formulation No. | 078 | 080 | 082 | 107 |
|---|---|---|---|---|
| KP-103 | 5.00 | 5.00 | 5.00 | 5.00 |
| alcohol | 19.35 | 20.00 | 59.998 | — |
| triacetin | 15.00 | — | — | — |
| glycerin | 35.00 | 24.998 | — | — |
| 1,3-butylene glycol | 25.00 | — | — | — |
| carbomer 980 | 0.50 | — | — | — |
| diisopropanolamine | 0.10 | — | — | — |
| Vitamin E | 0.05 | 0.002 | 0.002 | 0.05 |
| propylene glycol | — | 50.00 | — | — |
| cyclomethicone | — | — | 13.00 | — |
| diisopropyl adipate | — | — | 12.00 | 8.20 |
| myristyl lactate | — | — | 10.00 | — |
| isopropyl myristate | — | — | — | 5.48 |
| white petrolatum | — | — | — | 51.27 |
| urea | — | — | — | 30.00 |

Each of the formulations of Table 1 were spiked with tracer amounts of radiolabeled KP-103 at approximately 0.90 µCi/dose. A single clinically relevant dose (5 mg/cm2) was applied to dermatomed human skin obtained from one donor following elective surgery.

Percutaneous absorption was evaluated by mounting the dermatomed tissue in Bronaugh flow-through diffusion cells at 32 C. Six replicates were performed for each formulation. Fresh receptor fluid, PBS containing 0.1% w/v sodium azide and 1.5% Oleth-20, was continuously pumped under the skin at a nominal flow rate of 1 ml/hr and collected in 6-hour intervals. Following 24-hours of exposure, the residual formulation remaining on the skin surface was removed by repeated tape stripping (5 strips/cell). Subsequently, the epidermis was physically separated from the dermis by gentle peeling. The quantity of radioactivity in the tape-strips, epidermis, dermis, and receptor fluid samples was determined using liquid scintillation counting. The results for the calculated quantity of API collected in the receptor for each of the formulations of Table 1 are shown in FIG. 1.

As shown in FIG. 1, Formulations 080 and 107 demonstrated considerably higher skin penetration than did Formulations 078 and 082. Formulation 080 contains propylene glycol, a known skin-penetration enhancer, and exhibited a higher penetration through skin than any of the other formulations. Formulation 107 contains urea, a known skin-penetration enhancer, and exhibited the second highest skin penetration of the four formulations tested. Formulation 082 is a formulation according to the present invention and exhibited the lowest skin penetration of the tested formulations. Formulation 078 is a composition that is not within the scope of the invention and exhibited slightly higher penetration into and through skin than did Formulation 082. Of the four formulations, the formulation with the lowest level of skin penetration was formulation 082, the only formulation of the four that is a composition of the invention.

EXAMPLE 2

Nail Penetration Study

The formulations 078, 080, 082, and 107 of Example 1 were tested to determine penetration of the API from the formulation into and through nail plates. Each of the formulations of Table 1 was spiked with tracer amounts of radiolabeled KP-103 at approximately 0.90 µCi/dose. A clinically relevant protocol was followed, which entailed dosing 10 µL/cm² per day for 14 days onto healthy human finger nail plates, which were obtained from multiple donors.

Nail penetration was evaluated by mounting the finger nail plates into custom diffusion cells. Five replicates were performed for each formulation. A small cotton ball wetted with 0.1 mL normal saline was used as a receptor. For each day of the study, the surface of the nail was washed, and 10 µL of formulation was applied to the surface. Every second day, the cotton ball receptor was replaced. After fourteen days of exposure, the nail plate was sectioned into three sections, a central dorsal (upper) section, central ventral (lower) section and the remaining peripheral material. The quantity of radioactivity in the daily surface washes, cotton ball receptors, dorsal nail, ventral nail and peripheral nail was determined using liquid scintillation counting.

Figure 2:
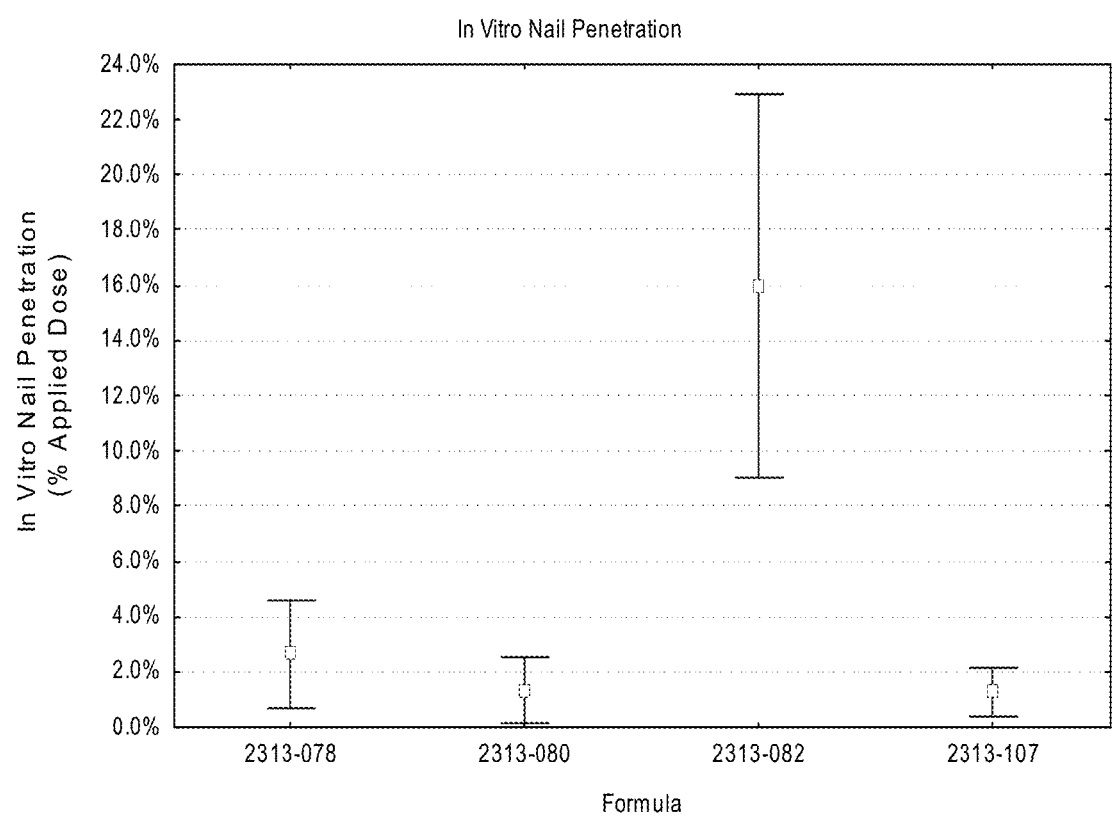
FIG. 2 is a graph showing the in vitro penetration of KP-103 through nail tissue from a formulation of the invention and from three prior art formulations.

The results are shown in FIG. 2. As shown in FIG. 2, the formulation of the invention, Formulation 082, provided over 6 times the penetration through the nail and into the saturated cotton ball receptor than did the other formulations, calculated as a percentage of the applied dose. The penetration of Formulations 080 and 107 had been expected to be highest through nail because they had exhibited a significantly higher penetration through skin. However, the penetration of API from Formulations 080 and 107 was, in fact, lower than from the other formulations even though these Formulations 080 and 107 contained well known skin penetration enhancers. This study establishes that the penetration of API from a formulation through skin is not predictive of the penetration of the API from the formulation through nail tissue. This study further establishes the unexpected ability of a preferred formulation of the invention, Formulation 082, to increase the penetration of API within the formulation through nail tissue.

EXAMPLE 3

Clinical Assessment in Animal Model of Onychomycosis

The efficacy of a formulation of the invention, Formulation 087, containing 3.00% w/w of a triazole antifungal API, KP-103, was evaluated in an animal model of onychomycosis and, in two separate studies, was compared with that of several commercial products intended for the treatment of onychomycosis. The composition of Formulation 087 is shown in Table 2.

TABLE 2

| FORMULATION 087 | |
|---|---|
| Component | Concentration (% w/w) |
| KP-103 | 3.00 |
| Alcohol | 60.00 |
| Vitamin E | 0.002 |
| Cyclomethicone | 13.00 |
| Diisopropyl adipate | 10.00 |
| Myristyl lactate | 13.998 |

In order to test the efficacy of Formulation 087 and the comparison products, onychomycosis was induced in six-week old Hartley guinea pigs. Each of Formulation 087 and the comparison products were tested in five animals. Two hundred (200) µL of a suspension of *Trichophyton mentagrophytes* SM-110 ($1\_10^8$ arthrospores/mL) was inoculated to the plantar and interdigital skin of the hind paws, and the entire feet were then covered with bandage. The bandage was removed 28 days after fungal inoculation. Test treatments were applied for a period of 30 days, starting on the 60th day after infection.

The infected nails were removed from the feet 7 days following the final treatment and were minced with scissors. The nails were placed in a glass homogenizer and PBS (phosphate buffer solution) containing 0.25% porcine pancreatic trypsin was added at a rate of 1 mL/50 mg of wet nail weight, and the nail was homogenized. The homogenate was allowed to stand at 37_C for 1 hour. One hundred microliters of the nail homogenate or its dilution was spread on a GPLP agar medium containing antibiotics and cultured at 30_C for 7 days. After culturing, the fungal colonies that appeared on the medium were counted, and the number of colony forming units (CFU) of fungi in the nails was calculated. The nail sample was considered culture-negative when no fungal colony appeared on the plate.

In Study 1, the efficacy of Formulation 087, applied to the nails at 30 µL/foot once a day for 30 days, was compared with untreated control animals and with 5% Amorolfine lacquer (Loceryl®) applied to the nails at 30 µL/foot once a week for 30 days. In Study 2, 1% naftifine gel (Naftin®) and 8% ciclopirox lacquer (Penlac®), each applied to the nails at 30 µL/foot once a day for 30 days, were compared with untreated control animals. The results of Study 1 and Study 2 are shown in Table 3.

TABLE 3

| Treatment | Mean no. of CFU in nails/foot after treatment (Log 10) | No. of feet with culture-negative nails/ total no. of feet (%) after treatment |
|---|---|---|
| Study 1 | | |
| Control (no treatment) | 29512 (4.47 +/− 0.37) | N/A |
| 5% Amorolfine lacquer (Loceryl ®) | 2398 (3.38 +/− 0.87) | 0/10 (0%) |
| Formulation 087 | 63 (1.80 +/− 0.53) | 6/10 (60%) |
| Study 2 | | |
| Control (no treatment) | 10964 (4.04 +/− 0.69) | N/A |
| 1% Ciclopirox lacquer (Penlac ®) | 214 (2.33 +/− 1.10) | 1/10 (10%) |
| 1% Naftifine gel (Naftin ®) | 501 (2.70 +/− 1.45) | 1/10 (10%) |

The data of Table 3 establishes that the formulation of the invention was more efficacious in treating onychomycosis in an animal model of human disease than were several currently available therapies for onychomycosis. With Formulation 087 of the invention, 60% of the infected nails were culture-negative following treatment. With the compositions of the prior art, 10% or less of the infected nails were culture-negative following treatment.

EXAMPLE 4

Clinical Assessment in Human Treatment

An adult male human suffering from onychomycosis of the left large toenail was treated daily by topical application of a 10% topical formulation of the invention containing KP-103. Additional components of the 10% topical formulation were alcohol, vitamin E, butylated hydroxytoluene, cyclomethicone, diisopropyl alcohol, and C12-15 alkyl lactates. Nail involvement at the initiation of treatment was 80% with onycholysis (separation of the nail plate from the nail bed) and thickening of subungual area. Following six months of treatment, the diseased proximal portion of the nail had grown out beyond the distal end of the nail plate (hyponychium) and was subsequently clipped off. There was no active fungal involvement of the nail plate, signs of onycholysis or thickening of the subungual area, or nail involvement after 6 months of treatment.

EXAMPLE 5

Additional Formulations of the Invention Containing KP-103

Several additional formulations of the invention were made containing identical components, but in varying concentrations, as shown in Table 4.

TABLE 4

| MATERIAL | FUNCTION | 10% SOLUTION | 5% SOLUTION | VEHICLE |
|---|---|---|---|---|
| Alcohol | vehicle | 56.73 | 59.85 | 63.04 |
| Cyclomethicone 5 | wetting agent | 12.30 | 13.00 | 13.67 |
| Diisopropyl adipate | non-volatile solvent | 11.36 | 12.00 | 12.62 |
| C12-15 alkyl lactate | non-volatile solvent | 9.46 | 10.00 | 10.52 |
| KP-103 | API | 10.00 | 5.00 | 0.00 |
| Vitamin E | anti-oxidant | 0.05 | 0.05 | 0.05 |
| Butylated hydroxytoluene | anti-oxidant | 0.10 | 0.10 | 0.10 |

While preferred embodiments of the invention have been described in detail, it will be apparent to those skilled in the art that the disclosed embodiments may be modified. It is intended that such modifications be encompassed in the following claims. Therefore, the foregoing description is to be considered to be exemplary rather than limiting, and the scope of the invention is that defined by the following claims.

The invention claimed is:

1. A method for the treatment of onychomycosis comprising topically applying to the surface of the nail of an individual suffering from onychomycosis a pharmaceutical composition comprising ethanol, diisopropyl adipate, C12-15 alkyl lactate, cyclomethicone, and (2R,3R)-2-(2,4-difluorophenyl)-3-(4-methylenepiperidine-1-yl)-1-(1H-1,2,4-triazole-1-yl)butane-2-ol;
    wherein the composition is formulated as a solution;
    wherein the ethanol is present in the composition at a concentration of at least 50% w/w;
    wherein the cyclomethicone is present in the composition at a concentration less than 25% w/w;
    wherein the diisopropyl adipate and C12-15 alkyl lactate are present in the composition at a total concentration between 15 and 50% w/w;
    wherein the concentration of (2R,3R)-2-(2,4-difluorophenyl)-3-(4-methylenepiperidine-1-yl)-1-(1H-1,2,4-triazole-1-yl)butane-2-ol in the composition is about 10% w/w; and
    wherein the application of the composition is in an amount and for a time sufficient to ameliorate the symptoms of the onychomycosis.

2. The method of claim 1, wherein the concentration of the cyclomethicone in the pharmaceutical composition is between 10% and 15% w/w.

3. The method of claim 1, wherein the pharmaceutical composition does not comprise a polymeric film forming compound.

4. The method of claim 1, wherein:
- the concentration of the ethanol in the pharmaceutical composition is at least 50% w/w;
- the concentration of the cyclomethicone in the pharmaceutical composition is between 10% and 15% w/w;
- the combined concentration of the diisopropyl adipate and the C12-15 alkyl lactate in the pharmaceutical composition is between 15% and 50% w/w; and
- wherein the pharmaceutical composition does not comprise a polymeric film forming compound.

* * * * *